Figure 1:
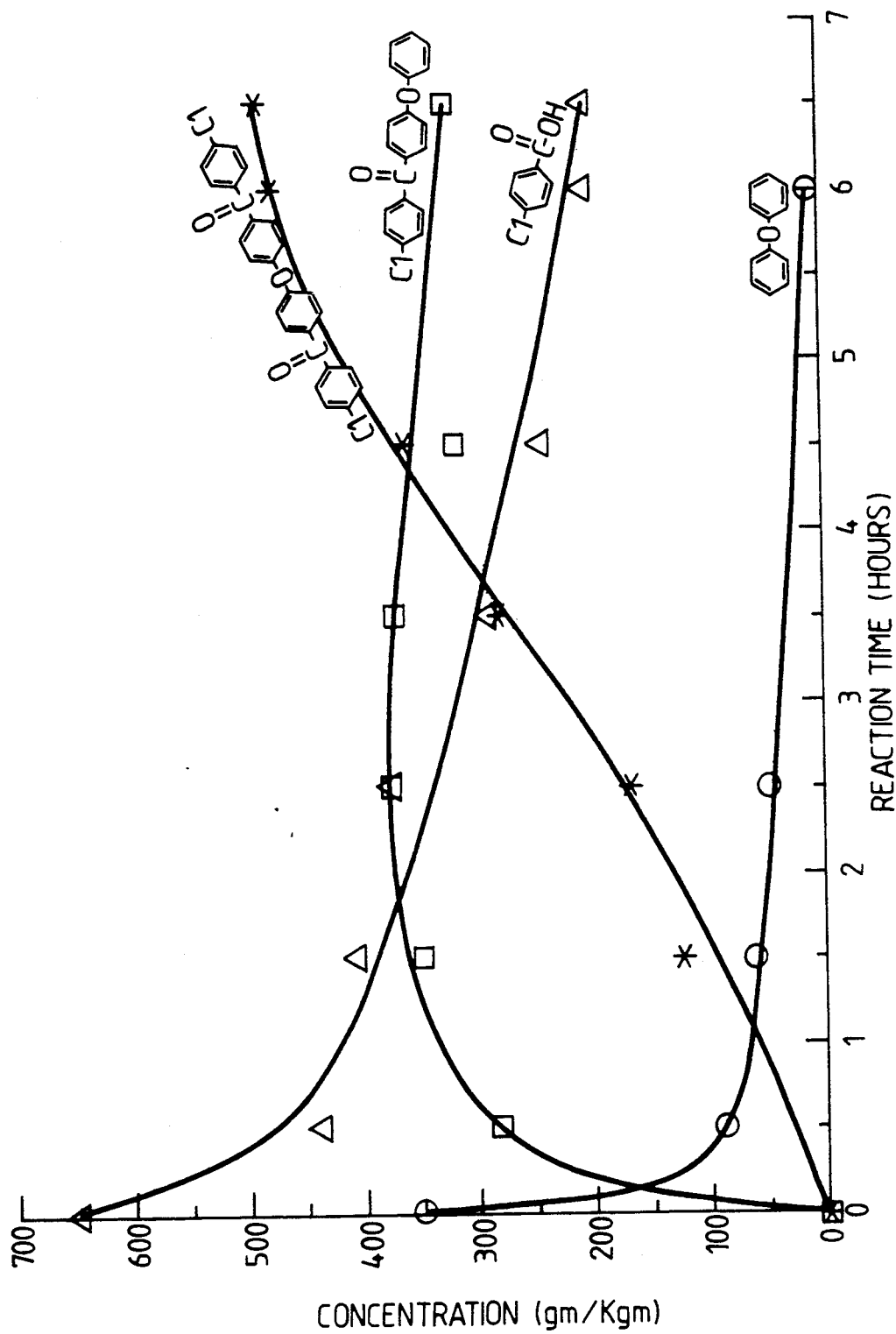

United States Patent [19]
Newton

[11] Patent Number: 5,164,527
[45] Date of Patent: Nov. 17, 1992

[54] PREPARATION OF AROMATIC COMPOUNDS

[75] Inventor: Alan B. Newton, Lealholm, England

[73] Assignee: Imperial Chemical Industries PLC, London, England

[21] Appl. No.: 680,147

[22] Filed: Apr. 3, 1991

[30] Foreign Application Priority Data

Apr. 4, 1990 [GB] United Kingdom ............... 9007577

[51] Int. Cl.$^5$ .............................................. C07C 69/76
[52] U.S. Cl. ........................................ 560/52; 560/64; 560/57; 560/53; 562/460; 562/403; 562/473; 562/45; 568/337; 568/332; 558/44; 558/56
[58] Field of Search ............... 560/52, 64, 57, 53; 562/460, 463, 473; 568/337, 332

[56] References Cited

U.S. PATENT DOCUMENTS

| | | | |
|---|---|---|---|
| 4,043,887 | 8/1977 | Pacifici | 560/52 |
| 4,853,398 | 8/1989 | Carr | 560/52 |
| 4,891,167 | 1/1990 | Clendinning | 560/52 |

FOREIGN PATENT DOCUMENTS 1919010 10/1970 Fed. Rep. of Germany .

Primary Examiner—Paul J. Killos
Attorney, Agent, or Firm—Cushman, Darby & Cushman

[57] ABSTRACT

Acylation or sulphonylation of aromatic compounds, one of which is selected from aromatic carboxylic and sulphonic acids and esters and anhydrides thereof, using an aluminosilicate catalyst having acidic sites.

16 Claims, 1 Drawing Sheet

PREPARATION OF AROMATIC COMPOUNDS

This invention relates to the preparation of aromatic compounds.

The use of aluminosilicate catalysts having acidic sites in the preparation of organic compounds is known. In particular, the use of zeolites as catalysts for the preparation of many organic compounds has been documented. A recent review paper, "Zeolites: Catalysts for Organic Syntheses", Wolfgang Holderich, Michael Hesse and Fritz Naumann, Angew. Chem. Int. Ed. Engl. 27(1988) 226-246, briefly explains the nature of zeolites and extensively reviews the possible reactions using zeolites. The advantage of using zeolites is well recognised in that they can usually be recovered and reused, possibly after regeneration, i.e. they are catalytic in nature; exhibit shape selectivity owing to their crystalline, porous structure which provides molecular-sized channels and/or cavities; and they often replace other reagents, such as a conventional Friedel-Crafts catalyst, which would normally be required in a given reaction and which may be expensive to obtain or remove. The paper mentions inter alia the use of zeolites for acylation reactions involving $C_1$–$C_{20}$ alkyl carboxylic acids and toluene, and involving benzene and phthalic anhydride to produce anthraquinone. EP-A-0316133 discloses using selected zeolites to catalyse the acylation reaction between diphenyl ether and terephthaloyl chloride to form 1,4-bis(4-phenoxybenzoyl)benzene. However, acid chlorides tend to be expensive, unstable and toxic and in the acylation reaction emit hydrogen chloride. FR-A-2 592 039 discloses using cerium exchanged zeolites to catalyse the acylation reaction between aliphatic carboxylic acids and aromatic hydrocarbons.

According to the present invention, a process for the preparation of aromatic compounds comprises reacting a first reactant selected from aromatic compounds having at least one hydrogen atom susceptible to electrophilic displacement and a second reactant selected from aromatic carboxylic and sulphonic acids and esters and anhydrides thereof in the presence of a naturally-occurring or synthetic zeolite having a 12-ring pore structure, capable of catalysing an acylation or sulphonylation reaction between said first and second reactants and under such conditions that the reaction occurs.

Preferably, said first reactant is a compound of formula I:

$$H^1-Ar-X \qquad \qquad I$$

wherein:
- $H^1$ is a hydrogen atom susceptible to electrophilic substitution;
- Ar is a divalent aromatic residue comprised of a single or multiple-ring or fused-ring system, the multiple rings being connected by a direct bond or by a linking group selected from —O—, —S—, —CR$_2$— wherein each R is independently —H or $C_1$ to $C_4$ alkyl, phenyl or the two groups R are joined externally to form a cycloaliphatic ring, —CO— or —SO$_2$—, provided that the or each linking group is selected or is located relative to $H^1$ such that $H^1$ is not deactivated to electrophilic substitution by the linking group; and
- X is —H, or, when Ar is a single ring, a para-directing group preferably selected from —OH or halogen, preferably —F, or alkoxy, e.g. —OCH$_3$, or, when Ar is a multiple-ring or fused-ring system, —H which may or may not be susceptible to electrophilic substitution or any other substituent group provided that $H^1$ is not deactivated thereby to electrophilic substitution.

Typical examples of said first reactant include diphenyl ether, phenol, halogenated benzene, e.g. fluorobenzene, naphthalene, biphenyl, meta-terphenyl, 1,3-diphenyl benzene, diphenyl sulphide, dibenzofuran and compounds of formulae:

HPhOPhOPhH
HPhOPhCOPhOPhH
HPhOPhC(CH$_3$)$_2$PhOPhH wherein Ph is 1,4-phenylene.

Preferably, said second reactant is selected from aromatic mono-carboxylic, di-carboxylic and sulphonic acids and esters and linear or cyclic anhydrides thereof. More particularly, the or each acid group or ester or anhydride thereof is attached to a phenylene moiety. Preferably, the esters are alkyl esters, particularly $C_1$–$C_6$ alkyl esters, and especially methyl esters. Preferably, the second reactant is a compound of formula I above in which $H^1$ and/or X is replaced by a carboxylic acid group, a sulphonic acid group or ester of the carboxylic or sulphonic acid. Typical examples of said second reactant include terephthalic acid, dimethyl terephthalate, benzoic acid, 4-hydroxybenzoic acid, isophthalic acid, naphthalene dicarboxylic acid, para-chlorobenzoic acid, para-methoxybenzoic acid, para-phenylbenzoic acid, para-nitrobenzoic anhydride, and para-toluene sulphonic acid.

One particularly useful combination of reactants according to the invention is diphenyl ether and terephthalic acid, dimethyl terephthalate or para-chlorobenzoic acid.

When, for example, the reactants are diphenyl ether and terephthalic acid, an excess of the first reactant, diphenyl ether, can function as the reaction solvent and minimise formation of higher condensation products. It will be readily apparent that, in some reaction systems, either an excess of the first or the second reactant can function as the reaction solvent or co-solvent and control the nature of the products. Additionally, other solvents or co-solvents, e.g. benzophenone or 1,2,4-trichlorobenzene, may be used.

It is also possible, in some instance, to subject the reaction mixture, after reaction has occurred, to a melt-fractionation process and thereby form a first phase, particularly a solid phase, enriched in the required product and a second phase, particularly a liquid phase, enriched in unreacted reactants and/or intermediates. The reactants and/or intermediates may then be recycled.

The reaction may be carried out at pressures above or below 1 bar. The reactants may be in the form of a gas, vapour or liquid. The resulting product may also be in the form of a gas, vapour or liquid.

The reaction products may include oligomeric and/or polymeric species.

Zeolites capable of effecting the reaction include both naturally-occurring and synthetic zeolites having a 12-ring pore structure and, more particularly, a multidimensional lattice structure which preferably is in the form of interconnected channels. Preferably, the zeolite is acidic in form, particularly in a transition-metal or rare-earth exchanged form, such as a iron or cerium exchanged form and, most preferably, in a substantially hydrogen-exchanged form, in which, preferably, at least 90% of the available cation sites are H+.

A preferred form of zeolite for use in the invention is zeolite beta which is more particularly described in U.S. Pat. No. 3,308,069, U.S. Pat. Re. 28,341, EP-B-0095304 and "The Framework Topology of Zeolite Beta", Higgins et al, Zeolites, 1988, Vol 8, November. Zeolite beta has a 12-ring pore structure and a multidimensional lattice forming interconnected channels.

The zeolite may be in form of a powder or granules or in the form of shaped particles, such as cylinders, or in the form of porous beads. In the reactions of the invention, the zeolite may be used in the form of a packed bed. As an alternative, a suspension of the zeolite in the reactor may be used.

The zeolite may be associated with an inorganic matrix which is preferably inert. The matrix may be present solely as a binding agent to hold particles of the zeolite together, or it may function as an inert diluent. Suitable inorganic matrices and diluents include conventional support materials such as silica, clays such as bentonites, synthetic porous materials such as silica-zirconia and aluminas.

The invention will now be illustrated by reference to the following Examples, and FIG. 1.

In Examples 1 to 10, 17 to 19 and 22 the reaction scheme proposed was:

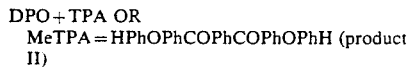
DPO+TPA OR
MeTPA = HPhOPhCOPhCOPhOPhH (product II)

wherein
DPO is diphenyl ether;
TPA is terephthalic acid;
MeTPA is dimethyl terephthalate; and
Ph is 1,4-phenylene;
but:

HPhOPhCOPhCOOX (product I)

wherein X is H or methyl is a possible product also.

EXAMPLE 1

11.53 g of a hydrogen-exchanged zeolite beta (available cation sites being 95% H+/5% Na+) having a $SiO_2/Al_2O_3$ ratio of 23 (zeolite beta being a large pore, i.e. 12-ring, zeolite) was subjected to an ion-exchange procedure by being immersed in 1M $NH_4Cl$, 10 ml/g of zeolite, at 60° C. for four hours. The zeolite was then filtered off the liquor, washed and dried overnight at 110° C. The exchange procedure was repeated. The zeolite was then calcined by heating to 120° C. over one hour, holding at 120° C. for one hour, raising the temperature to 550° C. over four hours and holding that temperature for sixteen hours. The yield of this process was 7.9 g of zeolite (available cation sites being 99.8% H+/0.2% Na+) with a $SiO_2/Al_2O_3$ ratio of 28.

1.0 g of the zeolite, DPO (53.5 g, 50 ml, 0.314 mole) and MeTPA (1.9 g, 0.010 mole) were stirred together in a flask, fitted with an air-cooled reflux condenser, under a slow stream of nitrogen. The contents of the flask were heated to reflux temperature and maintained at that temperature for four hours. The condensate was separated to remove water and any other volatiles. Any organic reactants present were returned to the reaction flask.

The progress of this reaction was monitored by analysing the exit gases from the condenser by infrared spectroscopy. The gases were passed via a trap held at −70° C. into the gas cell of the spectrometer. After one hour at reflux temperature, dimethyl ether was detected. The trap was then allowed to warm up to room temperature and methanol was detected.

The contents of the flask were filtered hot to remove the zeolite. Upon cooling, a white solid was deposited from the filtrate. Methanol was added to the filtrate and the deposited material was filtered off, washed with acetone and dried in a vacuum oven.

1.4 g of product having a melting point 201° C. to 208° C. was isolated. Fourier transform infrared spectroscopy (ftir) indicated the product as being substantially of product II, when compared to an ftir spectrum of product II obtained via another reaction route and identified by nuclear magnetic resonance (nmr) spectroscopy as being at least 98% product II. Nmr analysis of the isolated product was consistent with it being a mixture of products II and I in the ratio 93:5 with approximately 2% of higher oligomers. The nmr analysis only identified para-substituted products.

EXAMPLE 2

Example 1 was repeated using TPA (1.7 g, 0.010 mole) except that the reaction mixture was refluxed for three hours and that acetone was added to the reaction mixture instead of methanol after it had been cooled.

2.0 g of product having a melting point in the range 199° C. to 201° C. was isolated. Ftir indicated the product as being substantially of product II, when compared to an ftir spectrum of product II obtained via another reaction route and identified by nmr as being at least 98% product II. Nmr analysis of the isolated product was consistent with it being a mixture of products II and I in the ratio 70:30. The nmr analysis only identified para-substituted products.

The reaction was repeated and 1.37 g of product having a melting point in the range 207° C. to 213° C. was isolated.

EXAMPLE 3

Example 2 was repeated using the hydrogen-exchanged zeolite beta (available cation sites being 95% H+/5% Na+) and having a $SiO_2/Al_2O_3$ ratio of 23, of Example 1 prior to its being subjected to the further ion-exchange procedure.

1.34 g of product having a melting point in the range 197° C. to 206° C. was isolated.

EXAMPLE 4

Example 2 was repeated but using a hydrogen-exchanged zeolite Y having a $SiO_2/Al_2O_3$ ratio of 15.3 (zeolite Y being a large pore, i.e. 12-ring, zeolite). The product precipitated out of solution upon the addition of acetone.

0.45 g of product having a melting point in the range 201° C. to 217° C. was isolated and identified by ftir as being a mixture of products I and II.

EXAMPLE 5

Example 2 was repeated twice using MeTPA and TPA (quantities as for Examples 1 and 2), respectively, and a hydrogen-exchanged ZSM-5 zeolite having a large crystal size and having a $SiO_2/Al_2O_3$ ratio of 116

(zeolite ZSM-5 being a medium pore, i.e. 10-ring, zeolite), the reaction mixture being refluxed for eighteen hours.

In both instances, negligible reaction occurred.

EXAMPLE 6

Example 2 was repeated using a hydrogen-exchanged ZSM-5 zeolite having a small crystal size and having a $SiO_2/Al_2O_3$ ratio of 35.5.

Negligible reaction occurred.

EXAMPLE 7

Example 2 was repeated using a hydrogen-exchanged synthetic mordenite having a $SiO_2/Al_2O_3$ ratio of 17 (mordenite being a large pore, i.e. 12-ring, zeolite). The product precipitated out of solution upon the addition of acetone.

The reaction was minimal, 0.03 g of product being isolated.

EXAMPLE 8

Example 3 was repeated but using isophthalic acid instead of TPA. The reaction mixture was refluxed for four hours.

No solids separated on cooling the hot-filtered reaction mixture. Excess DPO was distilled off at 760 mm Hg pressure and the remaining mixture was diluted with petroleum ether. (The petroleum ether used was the fraction boiling between 40° and 60° C. at 1 bar pressure.) The resultant solid was filtered off the liquor, sucked dry and then washed with sodium hydroxide solution (1.0N) followed by water.

0.3 g of dried product having a melting point in the range 121° C. to 124° C. was isolated. Ftir, nmr and mass spectrometry (ms) indicated that the product was a mixture of:

$HPhOPhCOPh^1COOH$
$HPhOPhCOPh^1COPhOPhH$
$HPhOPhCOPh^1COPhOPhCOPh^1COOH$ wherein Ph is 1,4-phenylene and $Ph^1$ is 1,3-phenylene.

The alkaline washings were acidified and 1.0 g of a product having a melting point in the range 135° C. to 149° C. was isolated. Ir, nmr and ms indicated that the product was:

$HPhOPhCOPh^1COOH.$

EXAMPLE 9

Example 2 was repeated except that the reaction mixture was refluxed for eighteen hours.

3.0 g of product having a melting point in the range 200° C. to 208° C. was isolated.

The reaction was repeated using a reflux period of sixteen hours and 2.7 g of product having a melting point in the range 198.5° C. to 203° C. was isolated.

EXAMPLE 10

Example 2 was repeated except that the zeolite was replaced by a hydrothermally-treated amorphous aluminosilicate having a $SiO_2/Al_2O_3$ ratio of approximately 10.

0.2 g of product having a melting point in the range 229° C. to 350° C. was isolated. Analysis by ftir suggested the product was mainly:

$HPhOPhCOPhCOOH.$

EXAMPLE 11

30.0 g of zeolite (hydrogen-exchanged zeolite beta having a $SiO_2/Al_2O_3$ ratio of 23 and available cation sites being 95% $H^+$/5% $Na^+$), DPO (204 g, 1.2 mole) and 4-chlorobenzoic acid (CBA) (375.8 g, 2.4 mole) were placed in a flask, fitted with an air-cooled reflux condenser, and purged under a stream of nitrogen. The contents of the flask were heated and, when they became fluid, stirred continuously.

During the reaction, water co-distilled with the DPO and CBA. The water was removed and the organic reactants returned to the reaction flask. During the course of the reaction the temperature rose from 260° to 324° C. over a period of 6.5 hours (see Table 1).

TABLE 1

| Reaction Time (hours) | Reaction Temperature (°C.) |
|---|---|
| 0 | 260 |
| 1.0 | 270 |
| 1.5 | 282 |
| 2.0 | 284 |
| 2.5 | 288 |
| 3.5 | 302 |
| 4.0 | 304 |
| 4.5 | 309 |
| 5.0 | 314 |
| 6.0 | 316 |
| 6.5 | 324 |

Samples of reaction product were removed and analysed as follows. Initially each sample was filtered above 250° C. to remove the zeolite. Upon cooling solid was deposited. This solid was ground to form a representative sample. Thereafter a weighted amount of each sample was independently slurried in aqueous acetone and titrated with sodium hydroxide solution (1.0N) until a permanent end point to methyl orange was obtained. By this method the amount of CBA which had been consumed during the course of the reaction could be monitored.

Each slurry was then filtered. The solid was washed several times with water followed by acetone. It was then dried in a vacuum oven and weighed. Analysis of this product by nmr, ms and ftir suggested it was 4,4'-bis(4-chlorobenzoyl)diphenylether (CBDPE), product III

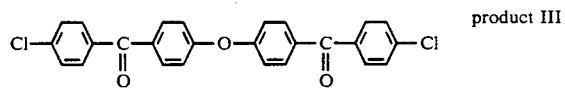

After recrystallisation, from 1,2 dichlorobenzene, product III was found to have a melting point in the range 251° to 251.6° C. High performance liquid chromatography indicated the product was 97.5% pure.

The aqueous acetone filtrate was diluted with water and insoluble matter was filtered off, washed with water, dried and weighed. Analysis of the product by ftir and ms was consistent with it being 4-(4-chlorobenzoyl)diphenylether (CPB).

Weighed amounts of the representative samples were also diluted with toluene and examined for diphenylether by capillary gas chromatography.

The reaction mixture contains essentially four species, the two organic reactants (CBA, DPO), 4-(4- chlorobenzoyl)diphenylether (CPB) and 4,4'-bis(4-chlorobenzoyl)diphenylether (CBDPE). The variation in concentration of these species as a function of reaction time is shown in FIG. 1 and given in tabular form in Table 2.

TABLE 2

| | Concentration (g/Kg) | | | |
|---|---|---|---|---|
| $R^N$ Time (Hrs) | Diphenyl Ether | 4-Chloro Benzoic Acid | 4-(4 Chlorobenzoyl) Diphenyl Ether | CBDPE |
| 0 | 352 | 648 | 0 | 0 |
| 0.5 | 89 | 438 | 283 | >107* |
| 1.5 | 62 | 407 | 350 | 125 |
| 2.5 | 49 | 375 | 377 | 169 |
| 3.5 | — | 290 | 373 | 282 |
| 4.5 | — | 243 | 318 | 363 |
| 6.0 | 9 | 204 | — | 477 |
| 6.5 | — | 204 | 325 | 488 |

*This sample contained some zeolite

EXAMPLE 12

Example 11 was repeated except samples were not withdrawn periodically. After 6.5 hours, the reaction mixture was filtered at 250° C. to remove the zeolite. The filtrate (A) was held at 200° C. in a partially crystalline state for 30 minutes. It was then filtered at 200° C. and gave a solid (B) and a filtrate (C). A, B and C were analysed by the method described in example 11. The results are given in Table 3.

TABLE 3

| | Weight Percent Abundance | | | | |
|---|---|---|---|---|---|
| | DPO | CBA | CPB | CBDPE | total |
| A | <1.0 | 20.4 | 32.5 | 48.8 | <102.7 |
| B | | 11.8 | 18.9 | 69.0 | 99.9 |
| C | | 26.7 | 41.8 | 33.6 | 102.1 |

These results show that melt-fractionation enables CBDPE to be enriched into the solid phase (B) and the reactants to be enriched into the liquid phase (C).

This is advantageous since it means the reactants and intermediate (CPE) can be recycled to the reaction flask for further reaction and purification can be achieved without recourse to a solvent crystallisation process.

EXAMPLE 13

Example 11 was repeated except the reaction was stopped after four hours and the zeolite was recovered by filtration at 250° C.

Example 11 was repeated again using the zeolite which had been recovered from the previous repeat. After a reaction time of 7 hours the reactor temperature was 293° C., lower than that reached in the original experiment, example 11, and the abundance of CBDPE and CPB was 78 and 350 g/Kg respectively, much lower than the amounts obtained in example 11, indicating the zeolite had lost part of its activity.

The zeolite was then recovered and calcined in air at 550° C. for 20 hours. The X-ray diffraction pattern of the calcined recovered zeolite was identical to that of the original zeolite.

Example 2 was repeated using this recovered calcined zeolite. 2.27 g of product were isolated compared to 2.38 g in the original example, i.e. there was little difference between the catalytic activity of the original zeolite and the recovered material which had been calcined.

EXAMPLE 14

1 g of zeolite (hydrogen-exchanged zeolite beta having a SiO$_2$/Al$_2$O$_3$ ratio of 23 and available cation sites being 95% H$^+$/5% Na$^+$), DPO (50 ml, 0.314 mole) and CBA (1.57 g, 0.01 mole) were stirred in a flask, fitted with an air-cooled reflux condenser, and purged under a stream of nitrogen. The contents of the flask were heated to reflux temperature and maintained at that temperature for 3 hours.

The contents of the flask were then cooled to room temperature and filtered to remove the zeolite. The filtrate was evaporated to a small volume and treated with a small volume of methanol where upon crystallisation occurred. The solid was filtered off, washed with a little methanol and dried in a vacuum oven.

2.0 g of a product having a melting point 121° to 122° C. was isolated. This is the same melting point range given for CPB in a paper by Radlemann et al, Makromol Chemie 1969, 130, 45.

A further 0.3 g of product was recovered from the methanol filtrate.

EXAMPLE 15

Example 14 was repeated except that CBA was replaced by 4-methoxybenzoic acid (10 mmole, 1.52 g).

The product was isolated by stripping off the excess DPO and recrystallising the residue from a toluene/propan-2-ol (about 40:60) mixture.

2.0 g of product having a melting point 143° to 144° C. was isolated. Analysis of the product by ftir was consistent with it being 4-(4-methoxybenzoyl)diphenylether.

EXAMPLE 16

Example 11 was repeated except that the following reactants were used, CBA (78.5 g), DPO (40.8 g), zeolite, as for example 11, (10 g) and benzophenone (200 g). After a reaction period of 4 hours the flask contents had reached a temperature of 307° C.

The reaction product was recrystallised from 1,2 dichlorobenzene and found to have a melting point in the range 250° to 251° C., consistent with it being product III. High performance liquid chromatography of the product indicated it was 99% pure.

EXAMPLE 17

5.1 g of a hydrogen-exchanged zeolite beta (available cation sites being 95% H$^+$/5% Na$^+$) having a SiO$_2$/Al$_2$O$_3$ ratio of 28 was subjected to an ion-exchange procedure by stirring with 51 ml of 0.1M cerium (III) chloride solution (solution adjusted to pH 6.0 using dilute aqueous ammonia) at 60° C. for four hours. This exchange was carried out three times, the zeolite being washed with deionised water and dried at 110° C. between each exchange. After the final exchange the zeolite was calcined in air at 550° C. for 16 hours. The resulting catalyst was analysed. It was found that 63% of the proton sites in the starting material had been exchanged by cerium. The SiO$_2$/Al$_2$O$_3$ ratio was 29.5.

Example 2 was repeated except that the zeolite used was the cerium exchanged material prepared above.

1.26 g of product having a melting point in the range 201° to 202° C. was isolated. This yield is lower than that achieved with the original zeolite beta catalyst in its acid form. Analysis of the product by ftir was consistent with it being a mixture of products II and I.

EXAMPLE 18

5.0 g of a hydrogen-exchanged zeolite beta (available cation sites being 95% H+/5% Na+) having a SiO$_2$/Al$_2$O$_3$ ratio of 23 was subjected to an exchange procedure by stirring, under nitrogen, with 8.34 g of ferrous sulphate heptahydrate in 100 ml of distilled water (solution adjusted to pH 2.0 using dilute sulphuric acid) at room temperature for seventeen hours.

The solid was filtered off in a nitrogen atmosphere. The solid was then washed five times with distilled water and subsequently dried in a vacuum oven. Elemental analysis showed the product contained 0.52 wt % iron and less than 0.02 wt % of residual sulphate.

Example 2 was repeated except the zeolite used was the iron exchanged material prepared above.

0.83 g of product was isolated. The product did not melt completely, even at a temperature of 300° C. Analysis of the product by ftir was consistent with it being a mixture of products I and II, with a high proportion of product I.

EXAMPLE 19

25.3 g of a hydrogen-exchanged zeolite beta (available cation sites being 95% H+/5% Na+) having a SiO$_2$/Al$_2$O$_3$ ratio of 23 was subjected to an ion-exchange procedure by stirring with a solution of NaCl (21.84 g) and NaOH (2.00 g) in 100 ml water at room temperature for four hours. This exchange was carried out twice, the zeolite being filtered, washed with deionised water and dried between each exchange. The resulting material was analysed. The composition of the material was Na 1.62, Al 2.32, Si 34.9 (w/w %), available cation sites being 82% Na+/18% H+. The SiO$_2$/Al$_2$O$_3$ ratio was 28.9.

Example 2 was repeated except that the zeolite used was the sodium exchanged material prepared above.

Negligible reaction occurred.

EXAMPLE 20

Example 3 was repeated except the terephthalic acid was replaced by 4-phenylbenzoic acid (1.98 g).

No crystalline material was obtained on cooling the filtered reaction mixture. Acetone was added to the mixture and, on standing overnight, white product crystals were obtained. The crystals were filtered off and washed with acetone, followed by dilute alkali, dilute acid, water and finally with acetone.

The product was dried in a vacuum oven. 1.5 g of product was isolated. Analysis of the product by ftir was consistent with it being an aromatic ketone.

EXAMPLE 21

Example 3 was repeated except the terephthalic acid was replaced by 4-nitrobenzoic anhydride (1.58 g).

0.5 g of crystals separated from the hot reaction mixture. These were identified as 4-nitrobenzoic acid.

The remaining reaction mixture was evaporated to a small volume which was then treated with methanol.

Solid crystalline product, weighing 1.03 g after drying, was isolated. This product had a melting point in the range 117.5° to 120° C.

Analysis of the product by ftir was consistent with it being nitrobenzoyl diphenylether.

EXAMPLE 22

Example 3 was repeated using a hydrogen-exchanged zeolite beta having a SiO$_2$/Al$_2$O$_3$ ratio of 75.

1.1 g of product having a melting point in the range 203° to 206° C. was isolated. Analysis of the product by ftir was consistent with it being a mixture of products I and II.

EXAMPLE 23

Example 1 was repeated except the MeTPA was replaced by p-toluene sulphonic acid monhydrate (3.8 g, 0.02 mole). The contents of the flask were heated to reflux temperature and maintained at that temperature for three hours.

The contents of the flask were cooled to about 50° C. and filtered to remove the catalyst. The filtrate was extracted with water. The aqueous phase was titrated with sodium hydroxide solution (1.0N) using a phenolphthalein indicator. A clear end point was observed, equivalent to 0.5 ml of base, showing that 97.5% of the toluene sulphonic acid had been consumed.

The organic phase crystallised on standing. The crystals were filtered off, washed with methanol and dried in a vacuum oven.

0.5 g of product having a melting point in the range 148.5° to 150.5° C. was isolated. This is consistent with the melting point for 4-methyl-4'-phenoxy-diphenylsulphone reported in papers by Passerini Gazz Chim Ital, 91, 223, (1961) and by Klages and Malecki, Anal Chem, 1966, 15, 691. Nmr of the isolated product was consistent with it being substantially product IV with a small amount of impurity.

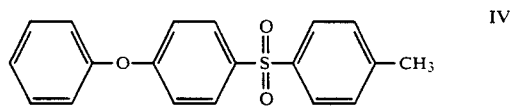

IV

The organic filtrate and washings were then distilled at atmospheric pressure to a small volume, treated with methanol. 1.8 g of product was isolated. This was dried in a vacuum oven. Analysis of it by nmr was consistent with it being substantially product IV.

EXAMPLE 24

Example 23 was repeated except no zeolite was used in the reaction. The filtrate was extracted with aqueous sodium chloride, rather than with water to minimise the formation of emulsions.

Titration with sodium hydroxide solution (1.0N) using a phenolphthalein indicator showed only 30% of the toluene sulphonic acid had been consumed.

No product crystallised from the organic phase on standing. After stripping off excess DPO from the filtrate and diluting with methanol, 0.86 g of product having a melting point in the range 123° to 140° C. was isolated. The nmr of the product was inconsistent with it being product IV.

I claim:

1. In a process for the preparation of aromatic compounds which comprises reacting a first reactant selected from aromatic compounds having at least one hydrogen atom susceptible to electrophilic displacement and a second reactant selected from aromatic carboxylic and sulphonic acids and esters and anhydrides thereof in the presence of a catalyst, the improvement wherein the catalyst is a naturally-occurring or synthetic zeolite having a 12-ring pore structure.

2. A process according to claim 1, in which said first reactant is a compound of formula:

$$H^1-Ar-X$$

wherein:

$H^1$ is a hydrogen atom susceptible to electrophilic substitution;

Ar is a divalent aromatic residue comprised of a single or multiple- or fused-ring system, the multiple rings being connected by a direct bond or by a linking group selected from —O—, —S—, —$CR_2$— wherein each R is independently —H or $C_1$ to $C_4$ alkyl, phenyl or the two groups R are joined externally to form a cycloaliphatic ring, —CO— or —$SO_2$—, provided that the or each linking groups is selected or is located relative to $H^1$ such that $H^1$ is not deactivated to electrophilic substitution by the linking group; and X is —H, or, when Ar is a single ring, a para-directing group selected from —OH, halogen and alkoxy, or, when Ar is a multiple-ring or fused-ring system, —H which may or may not be susceptible to electrophilic substitution or any other substituent group provided that $H^1$ is not deactivated thereby to electrophilic substitution.

3. A process according to claim 1, in which said second reactant is selected from aromatic mono-carboxylic, di-carboxylic and sulphonic acids and esters and linear or cyclic anhydrides thereof, the or each acid group, ester or anhydride thereof being attached to a phenylene moiety and the esters being alkyl esters.

4. A process according to claim 1, in which said second reactant is a compound of formula I defined in claim 2 in which $H^1$ and/or X is replaced by a carboxylic or sulphonic acid group or a carboxylic or sulphonic acid ester group.

5. A process according to claim 1, in which said first reactant is diphenyl ether and said second reactant is selected from terephthalic acid, an ester thereof and para-chlorobenzoic acid.

6. A process according to claim 1 in which the zeolite is in a substantially hydrogen-exchanged form.

7. A process according to claim 1 in which the zeolite is zeolite beta.

8. A process according to claim 1 comprises:

(i) reacting a first reactant selected from aromatic compounds having at least one hydrogen atom susceptible to electrophilic displacement and a second reactant selected from aromatic carboxylic and sulphonic acids and esters and anhydrides thereof in the presence of a naturally-occurring or synthetic zeolite having a 12-ring pore structure, capable of catalysing an acylation or sulphonylation reaction between said first and second reactants and under such conditions that the reaction occurs; and (ii) subjecting the reaction mixture to melt-fractionation to form a first phase enriched in product and a second phase enriched in reactants, whereby the reactants and/or any intermediates can be recycled.

9. In a process for carrying out an acylation reaction between an aromatic compound having at least one hydrogen atom susceptible to electrophilic displacement and an aromatic compound having at least one carboxylic acid group or ester or anhydride thereof in the presence of a catalyst, the improvement wherein the catalyst is zeolite beta.

10. In a process for carrying out a sulphonylation reaction between an aromatic compound having at least one hydrogen atom susceptible to electrophilic displacement and an aromatic compound having at least one sulphonic acid group or ester or anhydride thereof, in the presence of a catalyst, the improvement wherein the catalyst is zeolite beta.

11. The process of claim 1 wherein the zeolite catalyst has a multidimensional lattice structure.

12. The process of claim 11 wherein the zeolite catalyst has a multidimensional lattice structure and is in its acidic form, exchanged ions present being selected from the group consisting of hydrogen, transition-metal and rare-earth ions.

13. The process of claim 11 wherein the zeolite catalyst has a multidimensional lattice structure and is in its acidic form, exchanged ions present being selected from the group consisting of hydrogen, iron and cerium ions.

14. The process of claim 11 wherein the catalyst is zeolite beta or zeolite Y.

15. The process of claim 14 wherein the catalyst is in its acidic form, exchanged ions present being selected from the group comprising hydrogen, transition-metal and rare-earth ions.

16. The process of claim 1 wherein the reaction is carried out by mixing the reactants and the zeolite together and heating the resultant mixture to a temperature above ambient but not greater than the reflux temperature thereof.

* * * * *